United States Patent [19]

Baranowitz et al.

[11] Patent Number: 5,670,549
[45] Date of Patent: Sep. 23, 1997

[54] PREVENTION AND AMELIORATION OF LIVER TOXICITY WITH BETA-CAROTENE

[76] Inventors: Steven Baranowitz, 85 Tices La. - Apt. 39, New Brunswick, N.J. 08816; Paul F. Maderson, Box 6, 210 Axhandle Rd., Rd. 3, Quakertown, Pa. 18951

[21] Appl. No.: 497,538

[22] Filed: Jun. 30, 1995

Related U.S. Application Data

[63] Continuation of Ser. No. 141,264, Oct. 22, 1993, abandoned, which is a continuation of Ser. No. 978,870, Nov. 11, 1992, Pat. No. 5,260,340.

[51] Int. Cl.$^6$ .................................................. A61K 31/015
[52] U.S. Cl. ................................................... 514/763
[58] Field of Search ............................................. 514/763

[56] References Cited

U.S. PATENT DOCUMENTS

| | | |
|---|---|---|
| 4,159,340 | 6/1979 | Szmuszkovicz .................. 424/300 |
| 4,307,073 | 12/1981 | Nelson . |
| 4,314,989 | 2/1982 | Rosen et al. . |
| 4,435,427 | 3/1984 | Hoppe et al. . |
| 4,491,547 | 1/1985 | Seifter et al. . |
| 4,520,134 | 5/1985 | Rosen . |
| 4,681,897 | 7/1987 | Brand . |
| 4,713,398 | 12/1987 | Nonomura ..................... 514/725 |
| 4,730,007 | 3/1988 | Ehrenpreis . |
| 4,820,523 | 4/1989 | Shtohryn et al. . |
| 4,868,114 | 9/1989 | Nagasawa et al. . |
| 5,260,340 | 11/1993 | Baranowitz et al. ............. 514/629 |

FOREIGN PATENT DOCUMENTS

89/05637  6/1989  WIPO .

OTHER PUBLICATIONS

Ademoyero et al. Chemical Abstracts.
Oshima et al. Chemical Abstracts.
Chemical Abstracts 174463s, Ademoyero et al., 98:21, Sep. 27, 1983.
Chemical Abstracts 56093, Shoyakugaku Zasshi, 102:7, 5, Dec. 5, 1984.
McLean et al., *Biochemical Pharmacology* 24:37–42 (1975).
R.E. Bagdon et al., *Toxicology and Applied Pharmacology* 2:225–236 (1960).
Tapan K. Basu et al., *J. Clin. Biochem. Nutr.* 3:95–102 (1987).
I.A. Donatus, *Biochemical Pharmacology* 39(12):1869–1875 (1990).
J.C. Drummond et al., *J. Physiol.* 82:75–78 (1934).
Kenjiro Wake *Intl. Review of Cytology* 66(303):328–329 (1980).
93:10899r *Chem Abstracts* (1980).
98:174463s *Chem Abstracts* (1983).
108:36579h *Chem Abstracts* (1988).
109:224531f *Chem Abstracts* (1988).
111:19325s *Chem Abstracts* (1989).
114:214526x *Chem Abstracts* (1991).
114:136070c *Chem Abstracts* (1991).
M. R. Clemens et al., *Zeitschrift fur Ernahrungswissenschaft* 31:110–120 (1992).

*Primary Examiner*—Kevin E. Weddington
*Attorney, Agent, or Firm*—Darby & Darby

[57] ABSTRACT

A method for preventing acetaminophen toxicity in a mammal is provided. An acetaminophen toxicity inhibiting amount of beta-carotene is administered before, simultaneously with, after, or any combination thereof, administering acetaminophen to the mammal. Methods for reducing acetaminophen toxicity in a mammal in need of such treatment and for increasing the maximum amount of acetaminophen that can be administered to a mammal without the mammal exhibiting acetaminophen toxicity are also provided. Acetaminophen toxicity reducing amounts and acetaminophen toxicity preventing amounts, respectively, are administered. In another embodiment, a non-steroidal analgesic and anti-inflammatory composition of acetaminophen and an acetaminophen toxicity preventing amount of beta-carotene is provided.

2 Claims, No Drawings

PREVENTION AND AMELIORATION OF LIVER TOXICITY WITH BETA-CAROTENE

This is a continuation of application Ser. No. 08/141,264, filed Oct. 22, 1993 now abandoned, which is a continuation of application Ser. No. 07/978,870, filed Nov. 11, 1992, now U.S. Pat. No. 5,260,340.

FIELD OF THE INVENTION

The invention relates to a method for the prevention or the treatment of acetaminophen toxicity in a mammal in need of such treatment and to a method for increasing the maximum non-toxic dosages of acetaminophen that can safely be administered to a mammal. Beta-carotene is administered in appropriate amounts.

Compositions and dosage forms of acetaminophen with appropriate amounts of beta-carotene are disclosed as well.

BACKGROUND OF THE INVENTION

Acetaminophen is a commonly used, non-steroidal analgesic agent that is available in over one hundred prescription and over-the-counter formulations. While acetaminophen has fewer gastro-intestinal side effects than aspirin, another commonly used non-steroidal analgesic agent, acute and chronic acetaminophen toxicity can result in gastro-intestinal symptoms, severe liver damage, and even death.

The precise intermediates in the acetaminophen toxic metabolite pathway are not yet known. See, U.S. Pat. No. 4,520,134. It had been thought that when acetaminophen was ingested, the cytochrome P450 dependent enzyme system of the liver produced a potentially toxic metabolite of acetaminophen which was the cause of acetaminophen toxicity. It was further believed that when safe amounts of acetaminophen had been ingested, this toxic metabolite was cleared by hepatic glutathione stores. However in the case of acute or chronic overdose, excessive levels of the toxic metabolite were thought to deplete the glutathione stores in the liver, resulting in hepatic necrosis.

Based on the premise that cytochrome P450 was the agent that mediated the formation of the toxic metabolite, McLean et al., Biochemical Pharmacology 24:37–42, 1975, studied the effect of reducing the amount of cytochrome P450 on acetaminophen-induced hepatic necrosis. They concluded that dietary reduction of cytochrome P450 accompanied by reduction of glutathione did not necessarily diminish acetaminophen toxicity and that the effect of acetaminophen on yeast-fed rats could not be predicted from cytochrome P450 or glutathione levels. However, McLean et al. did find that increases in cytochrome P450 levels did increase acetaminophen toxicity. Therefore, one concludes from these studies that drugs that increase cytochrome P450 levels or concurrently decrease glutathione levels are contraindicated during acetaminophen therapy.

Later studies have proposed that acetaminophen induced hepatic necrosis may be due to cellular oxidative stress, resulting both in lipid peroxidation, protein and non-protein thiol oxidation, and changes in the intracellular calcium homeostasis. Donatus et al., Biochemical Pharmacology 39:1869–1875, 1990.

Symptoms of acute acetaminophen toxicity are typically mild or non-existent until at least 48 hours post-ingestion. In fact, in children under 12 years of age, acetaminophen toxicity is rarely fatal. Typically, only gastrointestinal irritability is observed in patients within 12–24 hours after ingestion of a large dosage of acetaminophen. Although gastro-intestinal symptoms may abate after 24 hours, liver function becomes abnormal. Hepatic failure occurs three to five days after ingestion, and after five days, either the hepatic toxic reaction resolves or death from hepatic failure occurs.

Typically, a dosage of about 140 milligrams per kilogram or more in a child or greater than 10 grams in an adult is toxic. These dosages have been observed to deplete the glutathione reserves of the liver. However, long term dosages as low as three grams per day have resulted in chronic liver disease. When ingestion exceeds 25 grams, mortality is significantly higher. However, the actual amount of acetaminophen that proves toxic depends upon the age, health, weight, sensitivity, and medical condition of the subject. For example, patients suffering from alcoholism, AIDS, or other diseases exhibit greater sensitivity to acetaminophen than do normal patients. The approximate half-life of acetaminophen is about 2½ hours when it is taken in normal dosages by a normal patient, but the half-life rises to over 4 hours when severe hepatocellular injury has occurred.

Present protocols for the treatment of acetaminophen toxicity include the induction of vomiting, stomach lavage, and/or the immediate administration of acetylcysteine to replenish the hepatic glutathione.

Rosen, U.S. Pat. No. 4,314,989, proposed to reduce the toxic effects of acetaminophen by administering methionine sulphate. The anti-toxin is preferably administered orally within about eight hours of acetaminophen ingestion. See also, U.S. Pat. No. 4,520,134.

Seifter et al., U.S. Pat. No. 4,491,574, reduced adverse side effects and toxicity due to aspirin by the administration of vitamin A and vitamin A precursors, such as beta-carotene, which yield vitamin A or a derivative thereof. Seifter et al. point out that an earlier study had shown that vitamin A could prevent duodenal ulcers and stress ulcers in rats fed 3-, 4-diaminotoluene, which they assert is chemically related to acetylaminophenol.

Nelson, U.S. Pat. No. 4,307,073, administered propylene glycol to alleviate acetaminophen toxicity, while Lamb, U.S. Pat. No. 4,681,897, added a capsaicinoid analgesic compound.

Chem Abstracts 93:108998r discloses the use of beta-carotene to prevent the toxic side effects of antibiotics in plants, and Chem Abstracts 98:174463s discloses the reduction of aflatoxin-induced liver toxicity in chickens by simultaneously administering beta-carotene.

Basu et al., J. Clin. Biochem. Nutr., 3:93–102, 1987, report that fourteen days of dietary beta-carotene supplement reduced cytochrome P450 as measured in mouse liver homogenates, but the authors offer no in vivo data.

Wake, International Review of Cytology, 66:303–353, 1980 describes four cell types found in the liver and the approximate volume occupied by each as hepatocytes (87%), endothelial cells (2.8%), Kupffer cells (2.8%), and stellate cells (1.4%). Bagdon, Toxicology and Applied Pharmacology 2:225–236, 1960, report that beta-carotene is deposited in, and remains sequestered in, only the Kupffer cells of the liver. The present inventors are unaware of any evidence that beta-carotene is stored in any other liver cells. Therefore, the present inventors do not believe that the results of the in vitro study reported by Basu et al. would be relevant in vivo. It is probable that the in vitro homogenization procedure used by Basu et al. would release beta-carotene from the Kupffer cells so that it would come in contact with hepatocytes, or more likely, fragments thereof. This would not occur in vivo. Furthermore, based upon the studies by McLean et al. discussed above, it would appear that a reduction in cytochrome P450 might result in a concurrent reduction in glutathione. This would, in turn, result in increased acetaminophen toxicity as was seen in McLean et al.

Nagasawa et al., U.S. Pat. No. 4,868,114, have found that the biosynthesis of glutathione can be stimulated by administering specific L-cysteine prodrugs.

It has now been discovered that acetaminophen toxicity can be prevented or reduced by the administration of beta-carotene. Furthermore, compositions and unit dosage forms have now been discovered that prevent acetaminophen toxicity and permit the administration to mammals of amounts of acetaminophen that were previously believed to be toxic, thereby increasing the therapeutic effects of the non-steroidal, non-narcotic analgesic agent, acetaminophen.

SUMMARY OF THE INVENTION

According to the present invention, there is provided a method for preventing acetaminophen toxicity in a mammal comprising administering an acetaminophen toxicity inhibiting amount of beta-carotene before, simultaneously with, after, or any combination thereof, administering acetaminophen to said mammal.

Further contemplated by the present invention are methods for reducing acetaminophen toxicity in a mammal in need of such treatment comprising administering an acetaminophen toxicity reducing amount of beta-carotene after administering acetaminophen to said mammal, and for increasing the maximum amount of acetaminophen that can be administered to a mammal without the mammal exhibiting acetaminophen toxicity comprising administering an acetaminophen toxicity preventing amount of beta-carotene before, simultaneously with, after, or any combination administering acetaminophen to said mammal.

In another embodiment, a non-steroidal analgesic composition con, rising acetaminophen and an acetaminophen toxicity preventing amount of beta-carotene is provided.

DETAILED DESCRIPTION OF THE INVENTION

Carotinoids are terpenes that are widely distributed in the plant and animal kingdoms. Beta-carotene is a common carotinoid having the chemical structure:

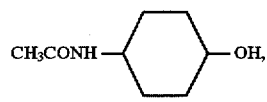

is an analgesic and antipyretic agent for moderate pain. Acetaminophen is a white bitter crystal composition that is soluble in water.

Prevention of acetaminophen toxicity is the prophylactic administration of beta-carotene to prevent any or all of the toxicological effects as described above of acetaminophen from occurring.

Reduction of acetaminophen toxicity is the amelioration, reversal, reduction, or any combination thereof of acetaminophen toxicity effects in an individual after acetaminophen administration that results in either chronic toxicity or acute toxicity, including acetaminophen overdose.

Increasing the amount of acetaminophen that can be administered to a mammal without producing acetaminophen toxicity enables those who have increased sensitivity to acetaminophen to tolerate normally non-toxic or even higher dosages of acetaminophen and allows those individuals to avail themselves of the full therapeutic effects of acetaminophen. Increasing the amount of acetaminophen that can be administered to an individual also permits those having normal sensitivity to acetaminophen to take increased dosages of acetaminophen, which would ordinarily produce toxic effects, without those toxic effects.

In all methods of the present invention, beta-carotene is administered systemically, i.e. other than topically, in safe, non-toxic amounts. Systemic administration includes both oral and parenteral routes. The preferred parenteral route is intravenous administration.

Beta-carotene is a component of a normal human diet, and the recommended daily requirement of beta-carotene for a normal adult human is about 3 mg. Although beta-carotene is provided through normal diet, the amounts of beta-carotene useful in the present invention typically can not be provided by normal diet. This is because the foods that supply beta-carotene in the normal diet contain various other substances. If sufficient amounts of these foods were consumed to provide the necessary amounts of beta-carotene, these other substances would be consumed in toxic amounts. Furthermore, approximately 25–75 percent of the carotenoids consumed in a normal diet are not absorbed and are

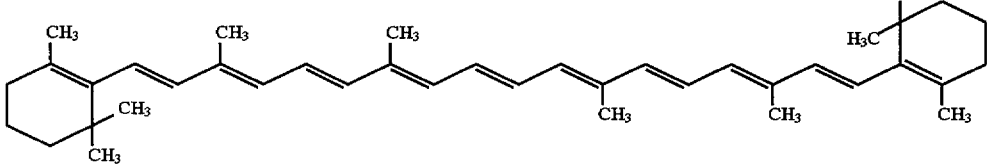

Beta-carotene, in mammals, readily undergoes oxidative cleavage at the central double bond to give two equivalents of retinal. Biochemical reduction of the aldehyde carbon yields vitamin A.

Although the safe upper limit of the amount of beta-carotene that can be administered to a human has not yet been determined, it is believed that such an upper limit is at least 1,000 mg/day.

Acetaminophen, excreted in the feces relatively unchanged. Therefore, beta-carotene is supplied in the methods of the present invention through supplementation. Commercially available forms of beta-carotene are available, for example, from Hoffman-LaRoche under the trademark SOLATENE™ or as "beta-carotene".

The amount of beta-carotene required to prevent acetaminophen toxicity is an acetaminophen toxicity inhibiting amount. This amount will depend upon the age, weight, sex, sensitivity, medical history, and the like of the individual. It will also depend upon the amount of acetaminophen in the individual's system. This amount of beta-carotene can be determined experimentally by methods well-known in the art such as by establishing a matrix of dosages and frequencies and assigning a group of experimental subjects to each point in the matrix. Typically for a normal adult human subject, this amount expressed as a weight ratio of beta-carotene to acetaminophen administered or to be administered to an individual will range from about 1:36 to about 3:2 and preferably from about 1:11 to about 1:1. Typical empirical amounts range from at least about 15 to about 325 mg of beta-carotene per 325 mg acetaminophen administered or to be administered to the individual. Most preferably, the empirical amount will range from about 30 to about 325 mg of beta-carotene per 325 mg of acetaminophen.

The amount of beta-carotene required to reduce acetaminophen toxicity in a mammal in need of such a treatment is an acetaminophen toxicity reducing amount. Again, that amount will depend upon the age, weight, sex, sensitivity, medical history and the like of the individual. Furthermore, it can be determined as above. Typically, for a normal, adult human subject, this amount expressed as a weight ratio of beta-carotene to acetaminophen administered to an individual will range from about 1:36 to about 3:2, and preferably from about 1:11 to about 1:1. Typical empirical amounts range from at least about 15 to about 325 mg of beta-carotene per 325 mg of acetaminophen administered to an individual. Most preferably, this empirical amount will range from about 30 to about 325 mg of beta-carotene per 325 mg of acetaminophen.

The amount of beta-carotene required to increase the maximum amount of acetaminophen that can be administered to a maximum without exhibiting acetaminophen toxicity is an acetaminophen toxicity preventing amount of beta-carotene. Again, that amount will vary as above. Furthermore, it can be determined as above. Typically for a normal adult human subject, this amount expressed as a weight ratio of beta-carotene to acetaminophen administered or to be administered to an individual will range from about 1:36 to about 3:2 and preferably from about 1:11 to about 1:1. Typical empirical amounts range from at least about 15 to 325 mg of beta-carotene per 325 mg acetaminophen administered or to be administered to the individual. Most preferably, the empirical amount will range from about 30 to about 325 mg of beta-carotene per 325 mg of acetaminophen.

Typically, the administration of beta-carotene will be within 48 hours of acetaminophen administration, whether before or after acetaminophen administration. Administration can be simultaneous as well. Furthermore, administration can be at any combination of times. In the case of treatment of acetaminophen toxicity, as in acute or chronic overdose, treatment should be commenced before liver effects are observable.

The compositions of the present invention include acetaminophen and an acetaminophen toxicity preventing amount of beta-carotene as described above. These compositions are non-steroidal analgesic and anti-pyretic due to the properties of the acetaminophen. Furthermore, a beta-carotene absorption adjuvant may be required. Such adjuvants include, but are not limited to, safflower oil.

The amount of beta-carotene in such compositions will depend upon the amount of acetaminophen in the composition. The amounts of each component can be determined as above, and the weight ratio of beta-carotene to acetaminophen will be as above. Special mention is made of compositions wherein the amount of acetaminophen ranges from about 50 parts by weight to about 98 parts by weight, and the amount of beta-carotene will range from about 2 parts by weight to about 50 parts by weight, based upon 100 parts by weight of acetaminophen and beta-carotene combined. When a beta-carotene adjuvant is used, up to about 20 grams of adjuvant can be used and the weight ratio of beta-carotene to acetaminophen is as above. In a preferred embodiment, the amount of acetaminophen will range from about 0.4 to about 95 and preferably about 33 to about 95 parts by weight, the amount of beta-carotene will range from about 0.001 to about 50 and preferably about 5 to about 50 parts by weight, and the amount of beta-carotene adsorption adjuvant will range from about 1 to about 99 and preferably about 1 to 33 parts by weight based upon 100 parts by weight of the three components combined.

These compositions can be formulated into unit dosage forms comprising the composition and a pharmaceutical acceptable vehicle as known to those of ordinary skill in the art. Furthermore, additives such as flavorings, colorants, disintegrants, and the like may be added. Unit dosage forms include, but are not limited to, capsules, caplets, tablets, and liquid forms. The amount of beta-carotene in such unit dosage forms will depend upon the amount of acetaminophen in the unit dosage form. The amount of each component can be determined as above. However, the amount of beta-carotene should be sufficient that if a quantity of unit dosage forms sufficient to provide a toxic amount of acetaminophen in the absence of beta-carotene (whether acute or chronic toxicity) were consumed by the individual, the amount of beta-carotene consumed concurrently would prevent or inhibit those toxic effects.

Typically, the amounts of acetaminophen, beta-carotene, and beta-carotene adsorption adjuvant will be as described above. The pharmaceutically acceptable vehicle will be present in an amount sufficient to deliver the active ingredients. Such amounts are known in the art.

Methods of preparation of these compositions and unit dosage forms are those conventional in the pharmaceutical arts.

DESCRIPTION OF THE PREFERRED EMBODIMENT

The following examples illustrate the invention without limitation.

The total amount of beta-carotene consumed by mice in each experiment was computed using the estimates that a 25 gram mouse will consume 5 mg/day of food and 25 ml/day of water, under normal conditions.

Prevention of Acetaminophen Toxicity (Pre-Administration)

EXAMPLE 1

Nine 129/ReJ mice, (The Jackson Laboratory-Bar Harbor, Maine) were pre-fed a diet of Modified HLR 341 with 10 percent of 10% beta-carotene beadlets, 1.6 mg/kg of vitamin K, and 4,000 IU/kg of vitamin A (Dyets, Inc.—Bethlehem, Pa.) for a period of five months. Each mouse ingested about 7.5 grams of beta-carotene.

Each mouse then received an intraperitoneal (IP) injection of 800 mg/kg of acetaminophen (Fisher Scientific—Pittsburgh, Pa.) dissolved in 20% Tween 80 (Sigma Chemical Company—St. Louis, Mo.) in saline. Seventy-two hours after injection, all mice were alive. Results are illustrated in Table 1.

Comparative Example 1A*,

Ten 129/ReJ mice (The Jackson Laboratory) were prefed a diet of Modified HLR 341 with 10 percent placebo beadlets, 1.6 mg/kg of vitamin K, and 4,000 IU/kg of vitamin A (Dyets, Inc.) for a period of five months.

Each mouse then received an IP injection of 800 mg/kg of acetaminophen (Fisher Scientific) dissolved in 20% Tween 80 (Sigma Chemical Co.). Seventy-two hours after injection, all of the mice had died. Results are illustrated in Table 1.

EXAMPLE 2

The procedure of Example 1 was followed using twenty mice pre-fed the diet for five weeks. Each mouse ingested about 1.75 grams of beta-carotene. Seventy-two hours after injection, thirteen of the mice were alive. Results are illustrated in Table 1.

Comparative Example 2A*,

The procedure of Comparative Example 1A*, was followed using twenty mice pre-fed the diet for five weeks. Seventy-two hours after injection, seven of the mice were alive. Results are illustrated in. Table 1.

EXAMPLE 3

The procedure of Example 1 was followed using twenty mice pre-fed the diet for twenty-three days. Each mouse ingested about 1.15 grams of beta-carotene. Seventy-two hours after injection, twenty of the mice were alive. Results are illustrated in Table 1.

Comparative Example 3A*

The procedure of Comparative Example 1A* was followed using sixteen mice pre-fed the diet for twenty-three days. Seventy-two hours after injection, all of the mice had died. Results are illustrated in Table 1.

EXAMPLE 4

The procedure of Example 1 was followed using nineteen mice pre-fed the diet for seven days. Each mouse ingested about 0.35 grams of beta-carotene. Seventy-two hours after injection, five of the mice were alive. Results are illustrated in Table 1.

Comparative Example 4A*

The procedure of Comparative Example 1A* was followed using nineteen mice pre-fed the diet for seven days. Seventy-two hours after injection, all of the mice had died. Results are illustrated in Table 1.

Prevention of Acetaminophen Toxicity
(Simultaneous Administration)

EXAMPLE 5

Four DBA/2J mice (The Jackson Laboratory) were weighed. Food was removed, and the mice were given drinking bottles containing a one percent aqueous solution of acetaminophen (Fisher Scientific) and 60 mg of beta-carotene per 100 ml ("Twinlab"—Twin Laboratories Ronkonkoma, N.Y.). After twenty-two hours, the mice were given a Modified HLR 341 diet having 10 percent of 10% beta-carotene beadlets, 10% safflower oil food pellets, 6% lard, 1.6 mg/kg of vitamin K, and 4000 IU/kg of vitamin A (Dyets, Inc.). Each mouse ingested about 20 mg total beta-carotene from the water and food by the twenty-fourth hour.

At the twenty-fourth and thirtieth hours, all of the mice received an IP injection of 500 mg/kg of acetaminophen dissolved in 20% Tween 80 (Sigma Chemical Co.) in saline. At the forty-eighth hour, all of the mice were weighed, and the drinking bottles were filled with pure water. Weights at the forty-ninth hour indicated that no mouse had eaten since the beginning of the experiment.

By the seventy-second hour, 75% of the mice were alive.

Comparative Example 5A*

Five DBA/2J mice (The Jackson Laboratory) were weighed. The, food was removed, and the mice were given drinking bottles containing a one percent aqueous solution of acetaminophen (Fisher Scientific). After twenty-two hours, the mice were given a Modified HLR 341 diet with 10% placebo beadlets, 10% safflower oil, 6% lard, 1.6 mg/kg of vitamin K, and 4000 IU/kg of vitamin A (Dyets, Inc.).

At the twenty-fourth and thirtieth hours all of the mice received an IP injection of 500 mg/kg of acetaminophen dissolved in 20% Tween 80 (Sigma Chemical Co.) in saline. At the forty-ninth hour, all of the mice were weighed, and the drinking bottles were filled with pure water. Weights at the forth-ninth hour indicated that no mouse had eaten since the beginning of the experiment.

By the seventy-second hour, all of the mice had died.

EXAMPLE 6

Ten 129/ReJ mice (The Jackson Laboratory) were starved for twelve hours during which time they lost 4% of their

TABLE 1

| | Comparison of Acetaminophen Toxicity in Beta-Carotene Pre-Fed and Placebo Pre-Fed Mice | | | | | | | |
|---|---|---|---|---|---|---|---|---|
| Example | 1 | 1A* | 2 | 2A* | 3 | 3A* | 4 | 4A* |
| Length of Pre-Feeding | 5 Months | 5 Months | 5 Weeks | 5 Weeks | 23 Days | 23 Days | 7 Days | 7 Days |
| Survival 72 Hours After Ingestion Survivors/Sample (%) | 9/9 (100) | 0/10 (0) | 13/20 (65) | 7/20 (35) | 20/20 (100) | 0/16 (0) | 5/19 (26) | 0/19 (0) |

Examples 1–4, when compared with Comparative Examples 1A*–4A*, respectively, demonstrate that administration of beta-carotene before challenge with toxic amounts of acetaminophen increases the survival rate significantly.

original weight. The mice were then given drinking bottles containing a 0.1% aqueous solution of acetaminophen (Fisher Scientific). The mice were given a Modified HLR 341 diet with 10 percent of 10% beta-carotene beadlets, 10% safflower oil, 6% lard, 1.6 mg/kg of vitamin K, and 4000

IU/kg of vitamin A (Dyets, Inc.). The food regimen was continued throughout the remainder of the experiment.

After twenty-four hours, the mice had regained or increased their original weight, and the drinking bottles were filled with a 0.5% aqueous solution of acetaminophen.

After the forty-eighth hour, weighing revealed maintenance of the mice's original weight, and each mouse received an IP injection of 600 mg/kg of acetaminophen (Fisher Scientific) dissolved in 20% Tween 80 (Sigma Chemical Co.) in saline.

At the sixtieth hour, all of the mice received an IP injection of 300 mg/kg of acetaminophen, and the drinking bottles were filled with pure water. At the seventy-second hour, all of the animals were alive. At the one hundred fiftieth hour 90% of the mice were alive, and they showed 93% of their original weights.

Comparative Example 6A*,

Ten 129/ReJ mice were starved for twelve hours during which time they lost 4% of their original weight. The mice were given drinking bottles containing a 0.1 percent solution of aqueous acetaminophen (Fisher Scientific). The mice were given a Modified HLR 341 diet with 10% placebo beadlets, 10% safflower oil, 6% lard, 1.6 mg/kg of vitamin K, and 4000 IU/kg of vitamin A (Dyets, Inc.). The food regimen was continued throughout the remainder of the experiment.

After twenty-four hours, the mice had regained or increased their original weights, and the drinking bottles were refilled with a 0.5% aqueous solution of acetaminophen with no beta-carotene.

After the forty-eighth hour, weighing revealed maintenance of the mice's original weight, and each mouse received an IP injection of 600 mg/kg of acetaminophen dissolved in 20% Tween 80 (Sigma Chemical Co.) in saline. At the sixtieth hour, all of the mice received an IP injection of 300 mg/kg of acetaminophen dissolved in 20% Tween 80 (Sigma Chemical Co.) in saline, and the drinking bottles were filled with pure water.

At the seventy-second hour, 80% of the mice were alive, and an the one hundred fiftieth hour, 50% of the mice were alive.

Antidotal Treatment of Acetaminophen Toxicity

EXAMPLE 7

The design of this experiment was predicated on the clinical time sequence involved in, or associated with, acetaminophen overdose and toxicity, and the biological response of mice to lethal injections of this drug. When a human ingests a toxic, potentially lethal dose of acetaminophen, few if any, clinical signs manifest during the first forty-eight hours. The patient remains alert and can take food voluntarily or by a nasal gastric tube. In contrast, it has been found than mice cease to feed following IP injection of a lethal dose of acetaminophen. Because the time course of human toxicity implies that a patient could orally ingest an antidote such as beta-carotene within the forty-eight hour period immediately following an overdose, it was proposed that a comparative animal model would be feeding subjects with a beta-carotene diet for forty-eight hours prior to the administration of a known lethal dose of acetaminophen.

Eight 129/ReJ mice (The Jackson Laboratory) were wholly or partially starved for seventy-two hours to enhance their appetite. Mean weight loss during this period was 13%. The mice were fed a Modified HLR 341 diet with 10 percent of 10% beta-carotene beadlets, 10% safflower oil, 6% lard, 1.6 mg/kg of vitamin K, and 4000 IU/kg of vitamin A (Dyets, Inc.) for forty-eight hours during which they showed a 98% restoration of their original weight. Each mouse ingested about 0.1 gram of beta-carotene by the forty-eighth hour.

The mice received IP injections of 800 mg/kg of acetaminophen dissolved in 20% Tween 80 (Sigma Chemical Co.) in saline, and seventy-two hours later, 63% of the mice were alive.

EXAMPLE 8

Twelve DBA/2J mice (The Jackson Laboratory) were weighed and starved for seventy-two hours. The mean weight loss during this time was 27%. The mice received a Modified HLR 341 diet with 10 percent of 10% beta-carotene beadlets, 10% safflower oil, 6% lard, 1.6 mg/kg of vitamin K, and 4000 IU/mg of vitamin A (Dyets, Inc.). The mice regained 86% of their original weight. Each mouse ingested about 0.1 gram of beta-carotene by the forty-eighth hour.

After forty-eight hours on the experimental diet, the mice received an IP injection of 800 mg/kg of acetaminophen (Fisher Scientific) dissolved in 20% Tween 80 (Sigma Chemical Co.) in saline. By thirty-six hours after the injection, one mouse had died.

The mice were reweighed, and a second injection of 600 mg/kg of acetaminophen dissolved in 20% Tween 80 in saline was given to each mouse. By seventy hours after the first injection, 92% of the mice were alive.

Comparative Example Art

Eleven DBA/2J mice (The Jackson Laboratory) were weighed and starved for seventy-two hours. The mean weight loss during this time was 27%. The mice were placed on a Modified HLR 341 diet with 10% placebo beadlets, 10% safflower oil, 6% lard, 1.6 mg/kg of vitamin K, and 4000 IU/kg of vitamin A (Dyets, Inc.). The mice regained 91% of their original weight.

After forty-eight hours on the diet, the mice received an IP injection of 800 mg/kg of acetaminophen (Fisher Scientific) dissolved in 20% Tween 80 (Sigma Chemical Co.) in saline. By thirty-six hours after the injection, one of the mice had died.

The mice were reweighed, and a second injection of 600 mg/kg of acetaminophen dissolved in 20% Tween 80 (Sigma Chemical Co.) in saline was given to each mouse. By seventy hours after the first injection, 50% of the mice had died.

The patents, test methods, and publications mentioned herein are hereby incorporated by reference.

Many variations of the present invention will suggest themselves to those skilled in the art in light of the above detailed description. All such obvious variations are within the full intended scope of the appended claims.

We claim:

1. A method for treating liver toxicity in a mammal in need of such treatment, said method comprising administering, to said mammal, an anti-liver toxicity effective amount of beta-carotene.

2. A method for preventing liver toxicity in a mammal in need of such treatment, said method comprising administering, to said mammal, a liver toxicity preventing effective amount of beta carotene.

* * * * *

UNITED STATES PATENT AND TRADEMARK OFFICE
CERTIFICATE OF CORRECTION

PATENT NO. : 5,670,549
DATED : September 23, 1997
INVENTOR(S) : Steven BARANOWITZ et al.

It is certified that error appears in the above-identified patent and that said Letters Patent is hereby corrected as shown below:

On the title page, Item [63], Related U.S. Application Data, change "Nov. 11, 1992" to --Nov. 19, 1992--.
Column 1, line 6, " Nov 11, 1992 " to -- Nov 19, 1992 --.

Signed and Sealed this

Twenty-seventh Day of January, 1998

Attest:

BRUCE LEHMAN

Attesting Officer

Commissioner of Patents and Trademarks